US010463794B2

(12) United States Patent
Riedel et al.

(10) Patent No.: US 10,463,794 B2
(45) Date of Patent: Nov. 5, 2019

(54) OPERATION AID FOR A MEDICATION DELIVERY DEVICE AND MEDICATION DELIVERY DEVICE COMPRISING AN OPERATION AID

(71) Applicant: SANOFI-AVENTIS DEUTSCHLAND GMBH, Frankfurt am Main (DE)

(72) Inventors: Stephan Riedel, Frankfurt am Main (DE); Stefan Wendland, Frankfurt am Main (DE); Stephen David Butler, South Staffordshire (GB); Mark Phillip Horlock, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/359,352

(22) PCT Filed: Nov. 26, 2012

(86) PCT No.: PCT/EP2012/073569
§ 371 (c)(1),
(2) Date: May 20, 2014

(87) PCT Pub. No.: WO2013/079429
PCT Pub. Date: Jun. 6, 2013

(65) Prior Publication Data
US 2014/0303562 A1 Oct. 9, 2014

(30) Foreign Application Priority Data

Nov. 29, 2011 (EP) ..................................... 11191211

(51) Int. Cl.
*A61M 5/20* (2006.01)
*A61M 5/24* (2006.01)

(52) U.S. Cl.
CPC ............ *A61M 5/2033* (2013.01); *A61M 5/20* (2013.01); *A61M 5/24* (2013.01); *A61M 2005/2006* (2013.01); *A61M 2205/586* (2013.01)

(58) Field of Classification Search
CPC .. A61M 3/0262; A61M 5/2425; A61M 5/282; A61M 5/178; A61M 5/2033;
(Continued)

(56) References Cited

U.S. PATENT DOCUMENTS 3,695,266 A 10/1972 Lussier
2003/0078912 A1* 4/2003 Oliver ................... A61M 31/00
(Continued)

FOREIGN PATENT DOCUMENTS

EP 0295917 12/1988
JP 2004-520892 A 7/2004
(Continued)

OTHER PUBLICATIONS

International Search Report and Written Opinion for Int. App. No. PCT/EP2012/073569, dated Jan. 30, 2013.
(Continued)

*Primary Examiner* — Lauren P Farrar
(74) *Attorney, Agent, or Firm* — Fish & Richardson P.C.

(57) ABSTRACT

The present disclosure relates to an operation aid for a medication delivery device, which is configured to alleviate the operation of an actuator of the medication delivery device. Furthermore, a system comprising a medication delivery device and an operation aid is disclosed.

14 Claims, 6 Drawing Sheets

(58) Field of Classification Search
CPC .. A61M 5/20; A61M 5/24; A61M 2005/2006; A61M 2205/586
See application file for complete search history.

(56) References Cited

U.S. PATENT DOCUMENTS

| | | | |
|---|---|---|---|
| 2004/0116873 A1* | 6/2004 | Fojtik ................... | A61M 5/007 604/221 |
| 2011/0144568 A1* | 6/2011 | Melsheimer ..... | A61B 17/00008 604/24 |
| 2013/0204197 A1* | 8/2013 | Bicknell ............. | A61M 5/3202 604/197 |

FOREIGN PATENT DOCUMENTS

| | | |
|---|---|---|
| JP | 2011-24687 A | 8/2012 |
| WO | 00/41754 | 7/2000 |
| WO | 2011/145998 | 11/2011 |
| WO | 2011/145998 A1 | 11/2011 |

OTHER PUBLICATIONS

Chinese Office Action for CN Application No. 201280067759.0, dated Feb. 5, 2016.
Japanese Office Action for Japanese Patent Application No. 2014-542873, dated Sep. 13, 2016.

* cited by examiner

OPERATION AID FOR A MEDICATION DELIVERY DEVICE AND MEDICATION DELIVERY DEVICE COMPRISING AN OPERATION AID

CROSS REFERENCE TO RELATED APPLICATIONS

The present application is a U.S. National Phase Application pursuant to 35 U.S.C. § 371 of International Application No. PCT/EP2012/073569 filed Nov. 26, 2012, which claims priority to European Patent Application No. 11191211.9 filed Nov. 29, 2011. The entire disclosure contents of these applications are herewith incorporated by reference into the present application.

TECHNICAL FIELD

The present disclosure relates to an operation aid for a medication delivery device.

BACKGROUND

Medication delivery devices are often activated by a button. As an example, in pen-type devices, the button may be placed at an end of the device. The button may be configured to be pressed by the thumb. This may be not very physiological, particularly when the user has to deliver a medication to another person. Furthermore, a certain force may be required for operating the button, wherein impaired users may have difficulties in applying the required force.

SUMMARY

It is an object of the present invention to provide an operation aid for a medication delivery device which may improve the handling of the medication delivery device. Furthermore, it is an object to provide a medication delivery device comprising an operation aid.

According to one aspect of the disclosure, an operation aid for a medication delivery device is provided, wherein the operation aid is configured to alleviate the operation of an actuator of the medication delivery device.

In particular, the operation aid may be used with a device comprising an actuator. In particular, the actuator may be configured to cause a delivery of a medication from the device, when the actuator is operated. As an example, when being operated, the actuator may move in an operation direction, for example in a direction along a longitudinal axis of the device. In particular, the operation aid may be configured to operate the actuator. Thereby, the operation of the operation aid may cause a delivery of a medication from the medication delivery device. Preferably, the actuator may be configured to be moved in a distal direction. The "distal direction" is a direction from a proximal end towards a distal end of the medication delivery device. The term "proximal end" designates that end of the device which is or is to be arranged furthest away from a dispensing end of the medication delivery device. The term "distal end" designates that end of the drug delivery which is or is to be arranged closest to the dispensing end of the device.

The operation aid may be configured to be used with an injection device. In a preferred embodiment, the operation aid may be suitable for a pen-type device. The medication delivery device may be an auto injector. The auto injector may be spring-loaded. In particular, the force required for delivering a medication may be provided by a spring.

In a preferred embodiment, the operation aid is ergonomically designed. Preferably, the operation aid is configured to improve haptic properties of the medication delivery device. The operation aid may be designed such that a handling of the medication delivery device by a user is simplified. The operation aid may be configured to be operated in different ways. For example, the user may use the index finger, the thumb or four fingers to operate the operation aid.

Preferably, the operation aid may facilitate an operation of the medication delivery device from a direction which is different from an operation direction of the actuator. Preferably, the operation aid may facilitate an operation of the device from a direction which is inclined to a longitudinal axis of the medication delivery device. For example, an operation from the side of the medication delivery device may be enabled.

The operation aid may comprise an actuation element. The actuation element may be configured to be operated by a user. The operation of the actuation element may cause a delivery of a medication.

In particular, the actuation element may be configured to cause an operation of an actuator of a medication delivery device. Thereby, the operation of the actuation element may cause a delivery of a medication from the medication delivery device. In particular, the actuation element may be configured to be operated instead of the actuator of the medication delivery device.

As an example, the actuation element may comprise a button. The button may be configured to be operated with a single finger. In a further embodiment, the actuation element may comprise a handle, in particular a lever. The handle may be configured to be operated with several fingers, for example with four fingers. Thereby, the actuation element may be easy to be operated by an impaired user.

The operation aid may comprise a longitudinal axis. The actuation element may be located at a longitudinal side of the operation aid. Thereby, the operation of the actuation element may be ergonomically improved compared to a direct operation of an actuator of a medication delivery device.

The operation aid may be configured to facilitate the actuation of a medication delivery device at a location of the operation aid or of the device which is different from a location of an actuator of the device. In particular, when the operation aid is attached to the device, the actuation element may be located at a different position than the actuator. Furthermore, a moving direction of the actuation element may differ from an operation direction of the actuator.

Furthermore, the operation aid may be configured to facilitate the actuation of a medication delivery device from a direction which is different from a moving direction of an actuator of the device.

The operation direction of the actuator may be a distal direction along a longitudinal axis of the medication delivery device. As an example, the operation aid is configured to facilitate the actuation of the medication delivery device from a direction which is inclined to the operation direction of the actuator, in particular perpendicular to the operation direction of the actuator. In a further embodiment, the operation aid may be configured to facilitate the actuation of the medication delivery device from a direction which is parallel to, but does not coincide with an operation direction of the actuator. In a further embodiment, the operation aid may be configured to facilitate the actuation of the medication delivery device from a direction which is coaxial to the operation direction of the actuator.

The actuation element may be in a basic position when the operation aid is not operated. The actuation element may be able to return to its basic position after it has been operated by a user.

For this aim, the actuation element may comprise a spring. The spring may be configured to hold the actuation element in its basic position when the actuation element is not operated by a user. The basic position of the actuation element may be a position with a distance to a body of the operation aid. Particularly, the actuation element may be positioned with a distance to a sleeve-shaped body. When a user operates the actuation element, the spring may be compressed. Thereby, the distance between the actuation element and the body of the operation aid may be diminished. When the user no longer operates the actuation element, the spring may relax and the actuation element may be moved back to its basic position.

Furthermore, the operation aid may comprise a grip, which may prevent a slipping-off of a hand of a user from the medication delivery device. The grip may comprise, for example, a coating. The coating may comprise a rubber material.

Preferably, the operation aid may be configured to allow a one-handed operation, in particular for dispensing a dose of a medication. In a further embodiment, a one-handed operation may be allowed for both "setting" and "dispensing" a dose of a medication.

Preferably, the operation aid comprises a handhold. The handhold may facilitate the handling of the medication delivery device, in particular a one-handed operation of the device. For example, a user may hold the handhold with two fingers. For example, the user may hold the handhold with his index finger and his middle finger, while he operates the operation aid with the thumb.

In a further embodiment, the handhold may comprise a strap-handle. The strap-handle may be configured such that the user may be enabled to hold a medication delivery device on the longitudinal side of the device. For example, the user may hold the medication delivery device by the strap-handle and operate the operation aid with his thumb.

In a preferred embodiment, the operation aid is attachable to the medication delivery device.

As an example, the operation aid may be configured to be imposed on a proximal end of the medication delivery device. Particularly, the operation aid may be configured to be located over the actuator of the medication delivery device. Preferably, the operation aid may at least partly cover the actuator of the medication delivery device.

Preferably, the operation aid comprises an attachment element. The attachment element may be configured to attach the operation aid to the medication delivery device.

The attachment element may comprise a sleeve. The operation aid may be attached to the medication delivery device by imposing the sleeve on a body of the medication delivery device. As an example, the sleeve may be configured to be imposed on a pen-type body of the device.

Furthermore, the attachment element may comprise a locking device for locking the operation aid to the device. For example, the operation aid may be snap-fitted to the medication delivery device. For example, a snap element, which may be a locking hook, may snap into a body of the medication delivery device, and thereby securely fix the operation aid to the body. In a further embodiment, the operation aid may comprise a rubber ring, which may be imposed on a body of the medication delivery device. Preferably, the rubber ring is dimensioned such that the operation aid may be fixed to the body of the medication delivery device.

In a further embodiment, the attachment element may comprise a thread. Preferably, the thread may be configured to fix the operation aid to the medication delivery device.

The operation aid may be detachable from the medication delivery device. In a further embodiment, the operation aid may be configured to be permanently fixed to the medication delivery device.

In a preferred embodiment, the operation aid is configured to reduce a force required to operate the medication delivery device. Preferably, the force may be reduced by providing a mechanical advantage. The amount of mechanical advantage may be adaptable by a user.

In a preferred embodiment, the operation aid comprises a transfer mechanism configured to transfer a movement of the actuation element into a movement of an actuator of a medication delivery device.

Preferably, the transfer mechanism may be configured to transfer a movement of the actuation element into a movement of the actuator when the actuation element is operated by a user. Preferably, the actuation element is connected to the transfer mechanism. The transfer mechanism may deflect the moving direction of the actuation element. In particular, the moving direction of the actuation element may differ from the moving direction of the actuator. Preferably, the transfer mechanism may transfer a force which is exerted on the actuation element to the actuator. Thereby, the actuator may be operated.

Preferably, the transfer mechanism comprises a transmitter element. In a preferred embodiment, the transmitter element is configured to operate the actuator of the medication delivery device when the actuation element is operated. In particular, the transmitter element may be configured to exert a force on the actuator, and thereby operate the actuator such that a medication is delivered. As an example, the transmitter element may push the actuator in a distal direction along a longitudinal axis of the medication delivery device. As an example, the transmitter element may comprise a bump. When the actuation element is in its basic position, the position of the transmitter element may be such that it does not exert a force on the actuator. The transmitter element may be configured to be positioned above the actuator.

In a further embodiment, the transfer mechanism may comprise at least one rod. Preferably, the transfer mechanism may comprise a plurality of rods.

The rods may be configured to transfer a movement of the actuation element to the actuator. The rods may be coupled by hinges. In one embodiment, the rods may be straight. In a further embodiment, the rods may be curved. The transfer mechanism may comprise both straight and curved rods. The rods may be coupled to the operation aid by at least one bearing. In one embodiment, the bearing may be a fixed bearing. In a further embodiment, the bearing may be a slide bearing. Preferably, at least one of the rods is connected to the actuation element. Furthermore, at least one of the rods may be connected to the transmitter element.

Preferably, the transfer mechanism of the operation aid may comprise a lever mechanism.

The lever mechanism may comprise at least one lever. The lever may be pivot-mounted. Preferably, the lever mechanism may lead to a reduction of a force required for operating the actuator. In particular, the lever mechanism may lead to a mechanical advantage. In a preferred embodiment, the transmitter element may be coupled to the lever.

The lever may transfer a movement of the actuation element to the transmitter element, such that the transmitter element may operate the actuator of the medication delivery device. Furthermore, the lever may be connected to the body of the operation aid, for example by a hinge.

In a further embodiment, the transfer mechanism of the operation aid may comprise a gear mechanism.

The gear mechanism may be configured to transfer a movement of the actuation element to a transmitter element. Preferably, the gear mechanism comprises at least one gear wheel. The gear mechanism may comprise at least one gear rod. Preferably, a first gear rod is connected to the actuation element. A second gear rod may be connected to the transmitter element. Preferably, the first and the second gear rods are in engagement with the gear wheel. The first gear rod may move, when the actuation element is operated by a user. Preferably, when the actuation element is operated and the first gear rod is moved, the gear wheel is rotated around a rotation axis. Because of the engagement of the second gear rod with the gear wheel, the second gear rod may be moved when the gear wheel is rotated. The rotation of the gear wheel may be such that the transmitter element is moved towards the actuator, when the actuation element is operated. The transmitter element may be moved towards the actuator until it may operate the actuator such that a medication may be delivered.

In a preferred embodiment, the actuation element is located at a distance from the transmitter element. In one embodiment, the actuation element may be located above the transmitter element. In particular, the moving direction of the transmitter element may be coaxial to the moving direction of the actuator. In a further embodiment, the actuation element may be located at a lateral distance from the transmitter element. In particular, the actuation element may be located such that the moving direction of the actuation element does not coincide with the moving direction of the transmitter element.

According to a further aspect of the present disclosure, a system is provided, the system comprising a medication delivery device and an operation aid.

The operation aid may comprise any structural and functional features as described above. The operation aid may be attachable to the medication delivery device, in particular to a body of the medication delivery device. In the system, the operation aid may be an element separate from the medication delivery device or may be attached to the medication delivery device. The medication delivery device may be configured to dispense a medication, in particular a medical fluid. Particularly, the medication may be insulin. The medication delivery device may be an injection device. The medication delivery device may be a pen-type device. The medication delivery device may be an auto injector.

The medication delivery device of the system may comprise an actuator. Preferably, the actuator may be configured to be operated by a user when the operation aid is not attached to the medication delivery device. As an example, the actuator may comprise a button. The medication delivery device may be configured to dispense a medication when the actuator is operated. In a preferred embodiment, the actuator is located at a proximal end of the medication delivery device.

In a preferred embodiment, the operation aid of the system may be configured to at least partly cover the actuator of the medication delivery device when the operation aid is attached to the medication delivery device. In particular, by covering the actuator, a direct operation of the actuator may be prevented.

In a preferred embodiment, the actuator may be configured to be moved along an axis in a distal direction of the medication delivery device. Preferably, the actuator is configured to be pushed in a distal direction to cause a dispensing of the medication.

Preferably, the operation aid is configured to cause a dispensing of the medication when the operation aid is attached to the medication delivery device. In particular, an operation of the operation aid may cause an operation of the actuator. Particularly, a user may operate the operation aid instead of directly operating the actuator.

According to a further aspect of the present disclosure, a medication delivery device comprising an operation aid is provided. The operation aid may be attached to a body of the medication delivery device and, thus, may be considered as a part of the medication delivery device. The medication delivery device and the operation aid may comprise any functional and structural features as described above.

The term "medication", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH-2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Further features, refinements and expediencies become apparent from the following description of the exemplary embodiments in connection with the figures.

Like elements, elements of the same kind and identically acting elements may be provided with the same reference numerals in the figures.

DETAILED DESCRIPTION

Figure 1A:
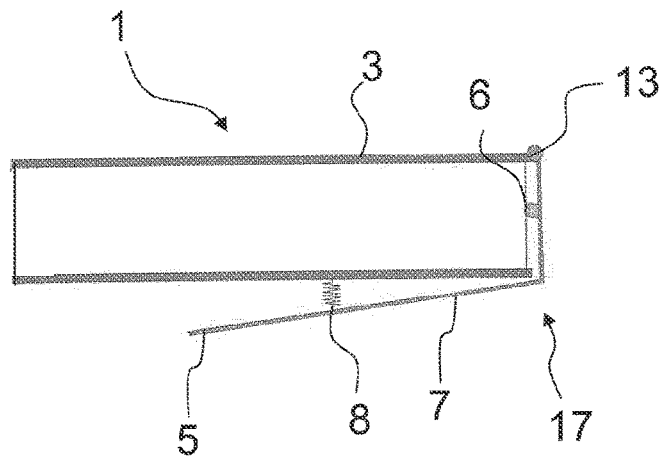
FIG. 1A shows an exemplary embodiment of an operation aid.

FIG. 1A shows an exemplary embodiment of an operation aid 1. The operation aid 1 comprises an attachment element 3. The attachment element may be configured to fix the operation aid 1 to a medication delivery device. The attachment element may comprise a sleeve. The sleeve may be configured to be imposed on the medication delivery device 2.

The operation aid 1 comprises an actuation element 5 operable by a user. The actuation element 5 may be configured to cause an operation of an actuator of a medication delivery device in order to dispense a medication from the medication delivery device. Accordingly, for dispensing a medicament, a user may operate the actuation element 5 of the operation aid 1 instead of directly operating the actuator of the medication delivery device. Thereby, the operation of the medication delivery device may be facilitated. As an example, the actuation element 5 may allow the operation of the medication delivery from a direction different than an operating direction of an actuator of the medication delivery device. Furthermore, the actuation element 5 may be located at a different position than the actuator of the device.

The actuation element 5 comprises a handle, in particular a lever 7. The lever 7 is connected to the attachment element 3 by a hinge 13. A spring 8 is arranged between the lever 7 and the attachment element 3. The actuation element 5 is located at a longitudinal side of the attachment element 3 such that the medication delivery device may be operated from a longitudinal side of the device.

Furthermore, the operation aid 1 comprises a transmitter element 6. The transmitter element 6 is configured to exert a force on an actuator of the medication delivery device, in order to deliver a medicament from the medication delivery device. The transmitter element may comprise, for example, a bump. Furthermore, the operation aid 1 comprises a transfer mechanism 17. The transfer mechanism 17 transfers a movement of the actuation element 5 to the transmitter element 6.

Figure 1B:
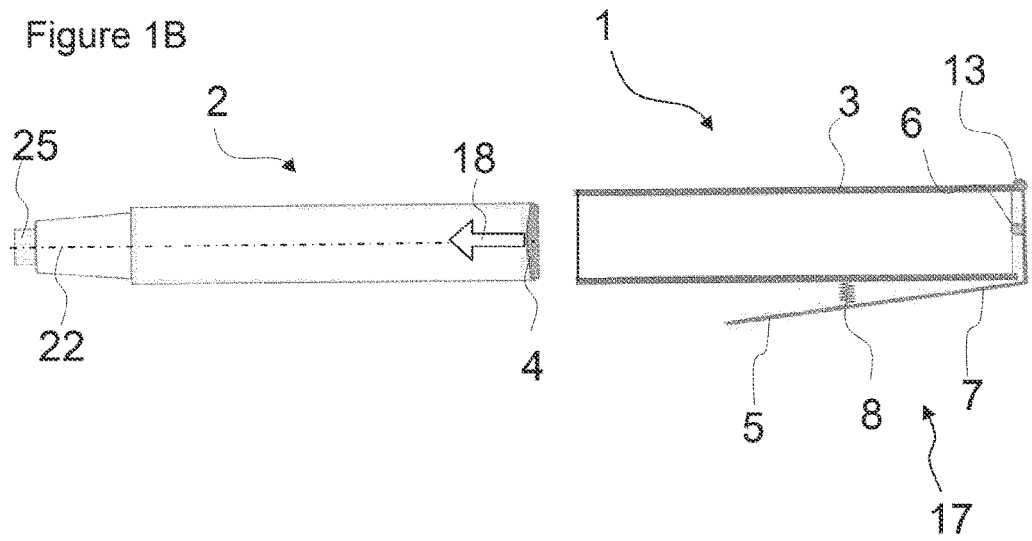
FIG. 1B shows how the operation aid of FIG. 1A is attached to a medication delivery device.

FIG. 1B shows the operation aid 1 of FIG. 1A and how it may be attached to a medication delivery device 2. By the medication delivery device 2 and the operation aid 1 a system is provided.

The medication delivery device 2 may be an injection device, for example a pen-type injector. In particular, the medication delivery device 2 may be an auto injector. The medication delivery device 2 is configured to dispense a medicament. The medicament may be a medical fluid. The medical fluid may be, for example, insulin.

The medication delivery device 2 comprises an actuator 4, which may be movable along a longitudinal axis 22 of the device 2. The actuator 4 comprises a button. The actuator 4 may be located at a proximal end of the medication delivery device 2.

The actuator 4 may be configured to be pushed in a moving direction 18. In particular, the medication delivery device 2 may dispense a medicament when the actuator 4 is activated. The medication delivery device 2 may dispense a medicament from a dispensing end 25. A needle may be attached to the dispensing end 25.

The operation aid 1 is configured to facilitate the use of the medication delivery device 2. For example, the operation aid 1 may facilitate the actuation of the medication delivery device 2 from a direction which is different from a moving direction 18 of the actuator 4. For example, the medication delivery device 2 may be actuated from a direction which is inclined to the longitudinal axis 22 of the medication delivery device 2.

The operation aid 1 may be attached to the medication delivery device 2 by inserting the medication delivery device 2 into the attachment element 3, in particular into the sleeve of the operation aid. In order to fix the attachment element 3 to the medication delivery device 2, the attachment element 3 may comprise a rubber ring. In another example, the attachment element 3 may be snap-fitted to the medication delivery device 2. For example, the attachment element 3 may comprise a locking hook which may snap into a body of the medication delivery device 2.

Figure 1C:
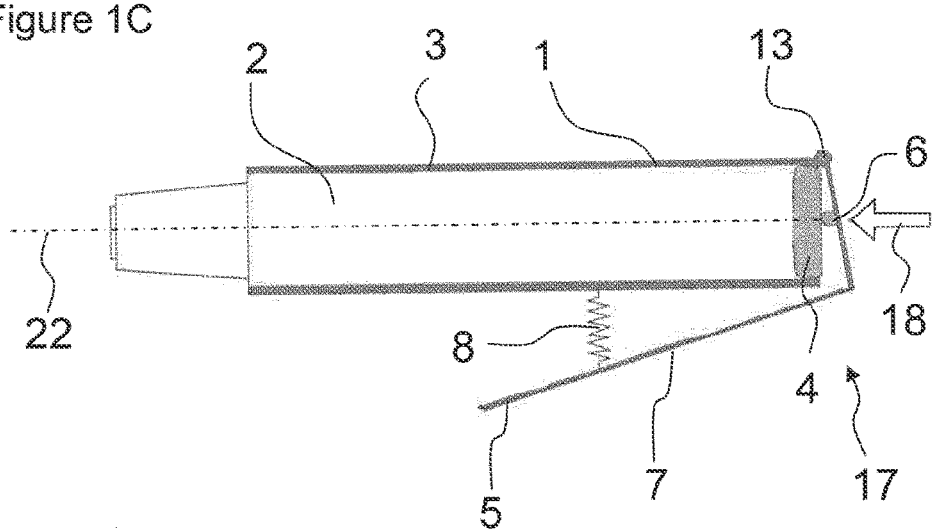
FIG. 1C shows the operation aid attached to the medication delivery device of FIG. 1B in a state when the operation aid is not operated.

FIG. 1C shows the operation aid 1 attached to the medication delivery device 2. The operation aid 1 at least partly covers the actuator 4 of the medication delivery device 2. The operation aid 1 is imposed on the medication delivery device 2 such that the transmitter element 6 is located over the actuator 4. The transmitter element 6 is configured to exert a force on the actuator 4 and, thereby, operate the actuator 4. In particular, the transmitter element 6 may operate the actuator 4 when the actuation element 5 is operated.

FIG. 1C shows the operation aid 1 attached to the device 2 in a condition where the actuation element 5 is not operated. The actuation element 5 is in a basic position. In this condition, the transmitter element 6 does not operate the actuator 4 of the medication delivery device 2. The spring 8, which is arranged between the lever 7 and the sleeve, is pretensioned in a way such that the lever 7 is held in its basic position. The basic position of the lever 7 may be such that one end of the lever 7, in particular the distal end, is held with a distance to the medication delivery device 2, respectively to the sleeve. For example, in the basic position, the lever 7 may extend in a direction being inclined to the longitudinal axis 22.

Figure 1D:
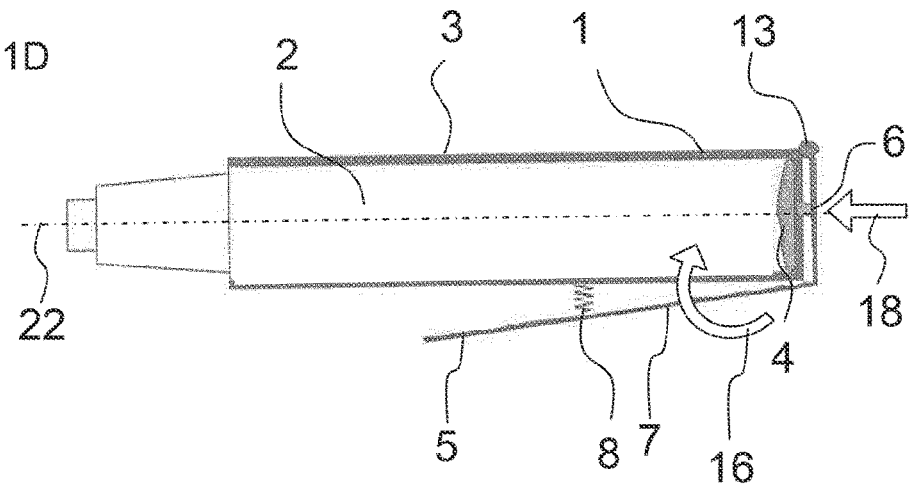
FIG. 1D shows the operation aid attached to the medication delivery device of FIG. 1B when the operation aid is operated.

FIG. 1D shows the operation aid 1 when the actuation element 5 is operated. The actuation element 5 may be operated by a user. The user may operate the actuation element 5 in different ways, for example with his index finger, with his thumb or with four fingers.

When the actuation element 5 is operated, the transmitter element 6 operates the actuator 4 of the medication delivery device 2. Thereby, a medicament may be delivered. In particular, the spring 8 is compressed and the lever 7 moves towards the medication delivery device 2, such that the angle between the lever 7 and the medication delivery device 2 decreases. The movement 16 of the lever 7 is such that it rotates around the hinge 13. When the lever 7 rotates around the hinge 13, the transmitter element 6 moves towards the actuator 4 of the medication delivery device, such that the transmitter element 6 exerts a force on the actuator 4. Thereby, the actuator 4 is operated. In particular, the actuator 4 is moved in a moving direction 18 along the longitudinal axis 22 by the transmitter element 6. Thereby, a medication is delivered from the medication delivery device 2.

Figure 2:
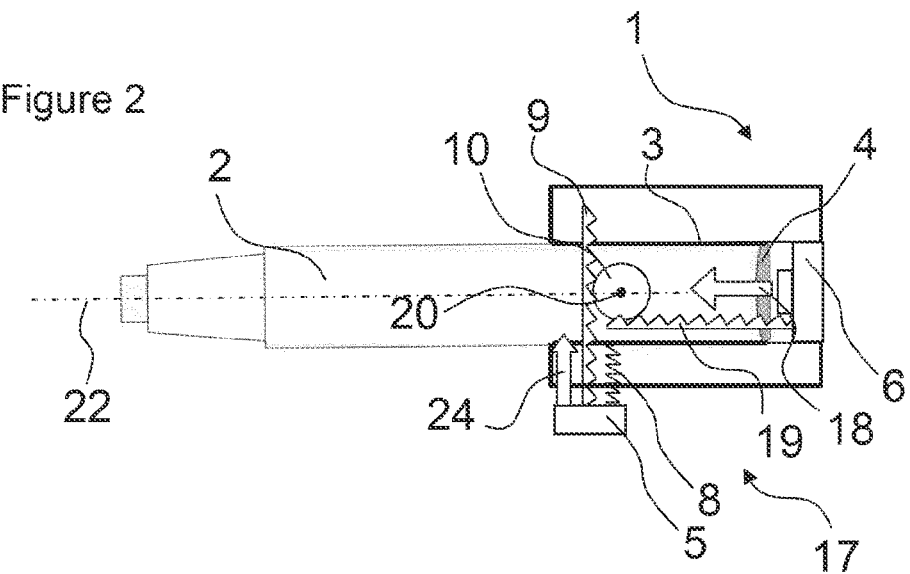
FIG. 2 shows a second embodiment of an operation aid attached to a medication delivery device.

FIG. 2 shows a further embodiment of an operation aid 1 attached to a medication delivery device 2. By the medication delivery device 2 and the operation aid 1 a system is provided. The operation aid 1 is configured to facilitate an actuation of the medication delivery device 2 from a direction which is inclined to, in particular perpendicular to, a longitudinal axis 22 of the medication delivery device. The operation aid 1 is attached to a proximal end of the medication delivery device 2. The operation aid 1 comprises an actuation element 5, located at a longitudinal side of the medication delivery device 2. The actuation element 5 has the shape of a button.

The operation aid 1 furthermore comprises a transmitter element 6. The transmitter element 6 is configured to operate an actuator 4 of the medication delivery device 2. A transfer mechanism 17, which is configured to transfer a movement of the actuation element 5 to the transmitter element 6, comprises gear rods 9, 19 and a gear wheel 10. The gear rod 9 is connected to the actuation element 5. Furthermore, the gear rod 9 is in engagement with the gear wheel 10. Another gear rod 19, which is connected to the transmitter element 6, is also engaged with the gear wheel 10. A spring 8 is arranged between the actuation element 5 and a sleeve 3 of the operation aid 1. The spring is pretensioned in a way such that the actuation element 5 is held in a basic position when the medication delivery device 2 is not operated.

When the actuation element 5 is pushed in an operation direction 24, the spring 8 is compressed and the actuation element 5 is moved towards the gear wheel 10. Thereby, the gear wheel 10 is rotated because of the engagement of the gear rod 9 with the gear wheel 10. When the gear wheel 10 is rotated, the transmitter element 6 is moved towards the actuator 4, because of the engagement of the gear rod 19 with the gear wheel 10. Thereby, the transmitter element 6 may operate the actuator 4, in particular push the actuator 4 in moving direction 18, and thereby a medication may be delivered from the medication delivery device 2. When the actuation element 5 is not operated by a user anymore, the spring 8 may relax and thereby move the actuation element 5 to its basic position.

Figure 3:
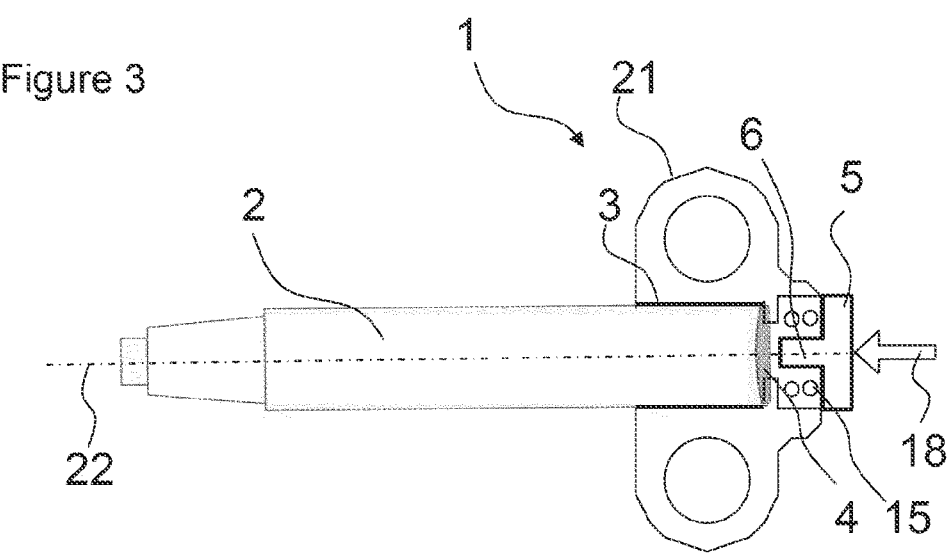
FIG. 3 shows a third embodiment of an operation aid attached to a medication delivery device.

FIG. 3 shows a further embodiment of an operation aid 1 attached to a medication delivery device 2. The operation aid 1 is imposed on a proximal end of the medication delivery device 2. The operation aid 1 comprises a handhold 21, which facilitates an easy handling of the medication delivery device 2. A user may hold the medication delivery device by the handhold 21 with two fingers. For example, the user may hold the handhold 21 with his index finger and his middle finger.

The operation aid 1 furthermore comprises an actuation element 5, which is located at the proximal end of the medication delivery device 2, a transmitter element 6 and a spring 15. The spring 15 is pretensioned in a way such that the actuation element 5 and the transmitter element 6 do not operate the actuator 4 when the actuation element 5 is not operated. When a user holds the medication delivery device 2 by the handhold 21, he may push the actuation element 5 with his thumb in a distal direction. Thereby, the spring 15 is compressed and the transmitter element 6 operates the actuator 4 of the medication delivery device 2. The moving direction 18 of the actuator 4 coincides with the distal direction. When the user does not push the actuation element 5 anymore, the spring may relax and the actuation element 5 is moved to a basic position.

In this embodiment of the operation aid 1, the moving directions of the actuation element 5 and the transmitter element 6 coincide with the moving direction 18 of the actuator 4.

Figure 4:
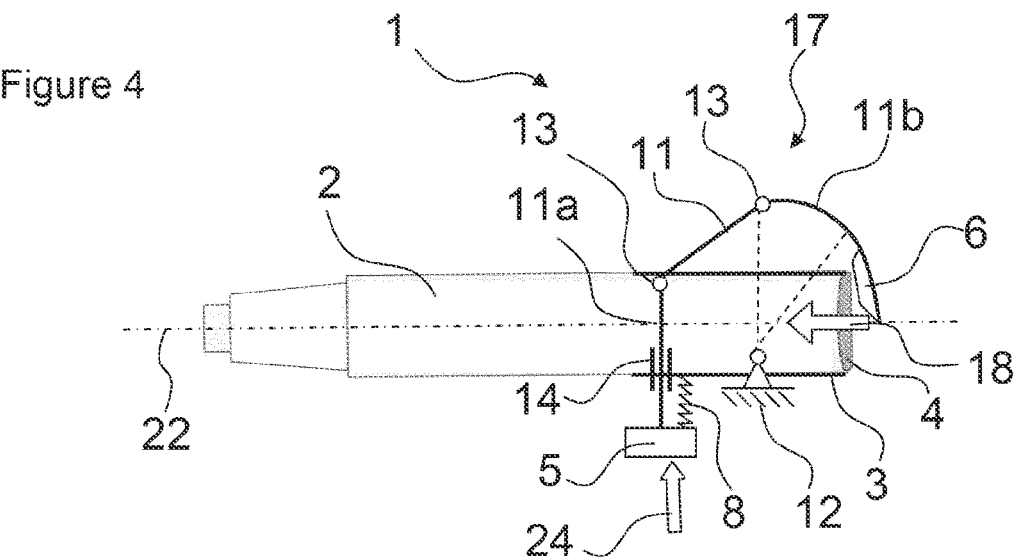
FIG. 4 shows a fourth embodiment of an operation aid attached to a medication delivery device.

FIG. 4 shows a further embodiment of an operation aid 1 attached to a medication delivery device 2. The operation aid comprises an actuation element 5 and a transmitter element 6. The actuation element 5 is located at a longitudinal side of the medication delivery device 2.

The operation aid 1 comprises a transfer mechanism 17. The transfer mechanism 17 comprises a plurality of rods 11, 11a, 11b, which are configured to transfer a movement of the actuation element 5 to the transmitter element 6. The rods 11, 11a, 11b are linked by hinges 13. A rod 11a is connected to the actuation element 5 and is bedded in a slide bearing 14. Another rod 11b is attached to the transmitter element 6. The rods 11, 11a, 11b may be straight or curved. The rods 11, 11a, 11b are coupled to the sleeve 3 by means of a bearing 12.

The actuation element 5 is held in a basic position by means of a spring 8. When a user operates the actuation element 5, the spring 8 is compressed, and the movement 24 of the actuation element 5 is transferred to the transmitter element 6 by means of the rods 11, 11a, 11b and the hinges 13. The transmitter element 6 laterally moves towards the actuator 4 of the medication delivery device 2, and pushes the actuator 4 in a moving direction 18 towards the distal end of the medication delivery device 2. When the user no longer operates the actuation element 5 the spring 8 may relax and the actuation element 5 is moved away from the medication delivery device 2 to its basic position. Thereby, the transmitter element 6 may be withdrawn from the actuator 4 of the medication delivery device 2.

Figure 5:
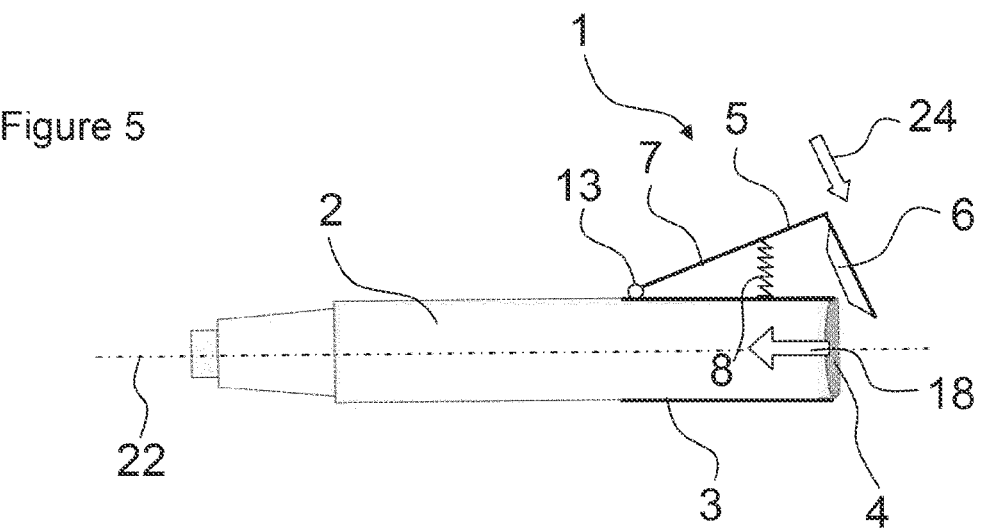
FIG. 5 shows a fifth embodiment of an operation aid attached to a medication delivery device.

FIG. 5 shows a further embodiment of an operation aid 1 attached to a medication delivery device 2. The operation aid 1 comprises an attachment element 3, an actuation element 5, a transmitter element 6, a spring 8 and a hinge 13. The actuation element 5 is located at a longitudinal side of the medication delivery device 2. The actuation element 5 comprises a lever 7. A spring 8 is arranged between the lever 7 and the sleeve 3. The spring 8 is pretensioned in a way such that one end of the lever 7, in particular a proximal end of the lever 7, is held with a distance to the attachment element 3, respectively to the medication delivery device 2 when the operation aid 1 is not operated.

When a user moves the actuation element 5, respectively the lever 7, in a moving direction 24, the spring 8 is compressed and the lever 7 rotates around the hinge 13. Thereby the transmitter element 6 moves towards the actuator 4, until the transmitter element 6 operates the actuator 4, in particular pushes the actuator 4 in a distal direction, such that a medication is delivered from the medication delivery device 2. When the user does not operate the actuation element 5 anymore, the spring 8 is enabled to relax, and the lever 7 is moved away from the attachment element 3, in particular from the sleeve. Thereby, the transmitter element 6 may be withdrawn from the actuator 4.

Figure 6:
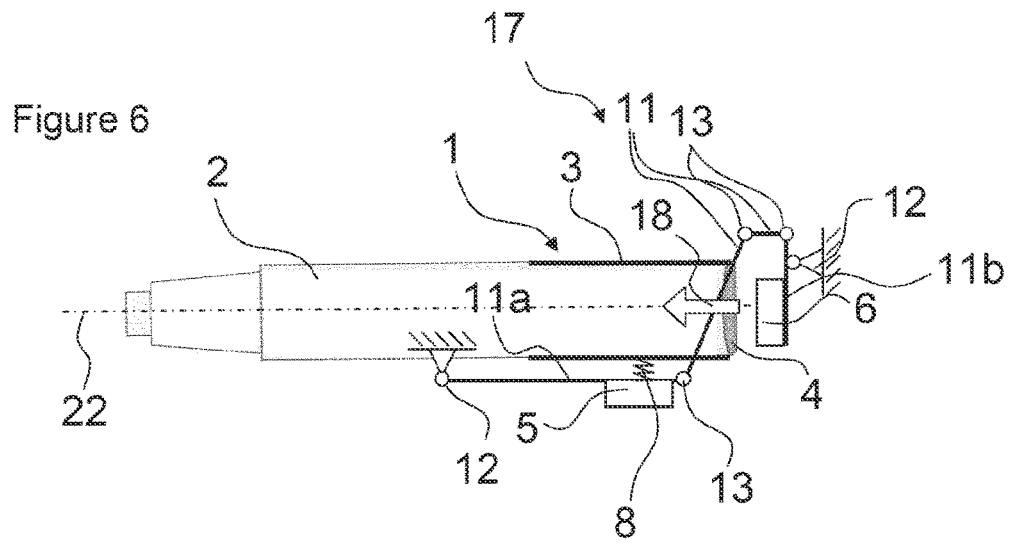
FIG. 6 shows a sixth embodiment of an operation aid attached to a medication delivery device.

FIG. 6 shows a further embodiment of an operation aid 1 attached to a medication delivery device 2. The operation aid 1 comprises an actuation element 5, which is located at a longitudinal side of the medication delivery device 2, a transmitter element 6, and a transfer mechanism 17. The transfer mechanism 17 comprises a plurality of rods 11, 11a, 11b and a plurality of hinges 13. The rods 11, 11a, 11b are coupled to the attachment element 3 by bearings 12. One rod 11a is connected to the actuation element 5. Another rod 11b is connected to the transmitter element 6. When a user operates the actuation element 5, the movement of the actuation element 5 is transmitted to the transmitter element 6 by the rods 11, 11a, 11b and the hinges 13. Thereby, the transmitter element 6 is moved in a distal direction such that it operates the actuator 4. A spring 8 is arranged between the actuation element 5 and the attachment element 3, which is pretensioned in a way such that the actuation element 5 is held in a basic position when the medication delivery device 2 is not operated.

Figure 7:
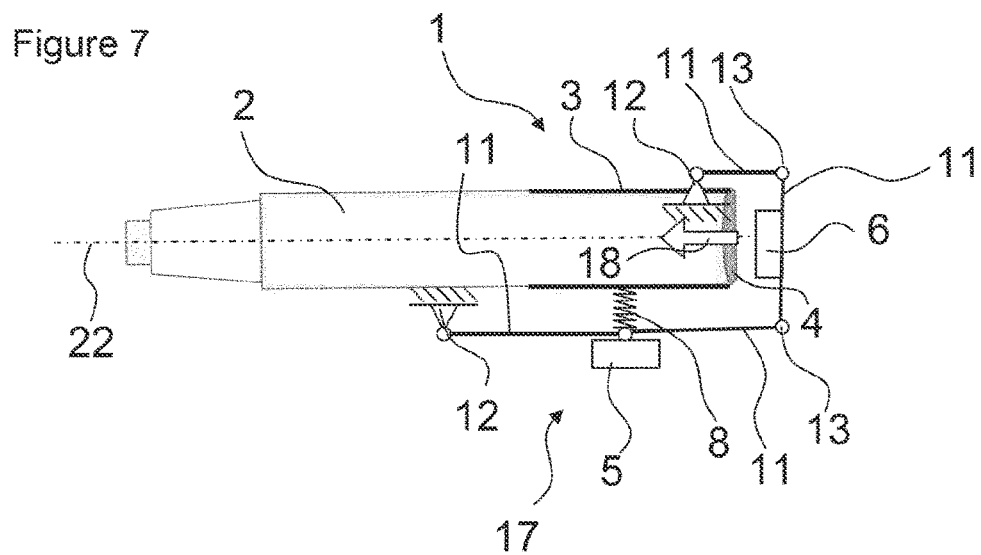
FIG. 7 shows a seventh embodiment of an operation aid attached to a medication delivery device.

FIG. 7 shows a further embodiment of an operation aid 1 attached to a medication delivery device 2, which is similar to the embodiment of FIG. 6, besides that the rods 11 are arranged in a different way. However, the mechanism works likewise.

Figure 8:
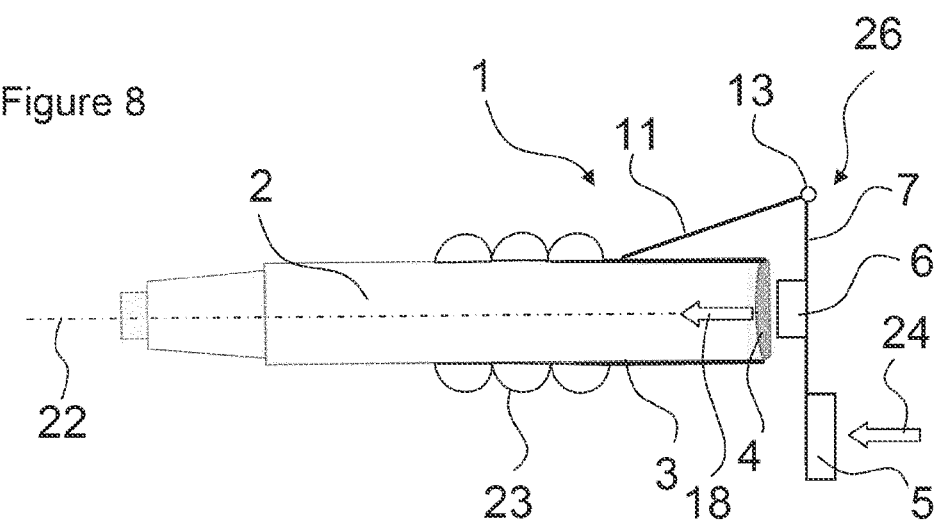
FIG. 8 shows an eighth embodiment of an operation aid attached to a medication delivery device.

FIG. 8 shows a further embodiment of an operation aid 1 attached to a medication delivery device 2. The operation aid 1 comprises an actuation element 5, a transmitter element 6, a rod 11, a lever 7 and at least one hinge 13. The lever 7 is movable around the hinge 13. The actuation element 5 and the transmitter element 6 are located at the lever 7. The transmitter element 6 is arranged on a longitudinal axis 22 above the actuator 4 of the medication delivery device 2. The actuation element 5 is located at a lateral distance from the transmitter element 6, such that the actuation element 5 is not arranged on the longitudinal axis 22. The actuation element 5 and the transmitter element 6 are coupled by a lever mechanism 26. By the lever mechanism 26, a mechanical advantage between the actuation element 5 and the transmitter element 6 is achieved. Because of the mechanical advantage, the force required to operate the actuator 4 of the medication delivery device 2 is reduced, compared to an embodiment of the medication delivery device 2 without an operation aid 1. The mechanical advantage may be adapted by the user, such that the force which is required to operate the actuator 4 may be reduced or increased. In particular, the length of the lever arm, i. e. the distance between the actuation element 5 and the hinge 13 can be adjusted by the user.

In this embodiment, the direction of the force which has to be applied by the user is parallel to the moving direction 18 of the actuator 4. However, the actuation element 5 is laterally displaced from the actuator 4 such that the point of application of the force is shifted by the operation aid 2. This embodiment may be particularly suited for impaired users which may have difficulties in applying the force required to operate the actuator 4.

Additionally, a grip 23 is arranged on the medication delivery device 2, which facilitates the handling of the medication delivery device 2. The grip 23 may be such that the user may dispense a medicament by using a single hand. For example, the grip may comprise openings into which a user may put his fingers or a strap handle. The user may hold the medication delivery device 2 with three fingers and operate the actuation element with his thumb.

The invention claimed is:

1. A system comprising: an operation aid and a medication delivery device, the medication delivery device having an actuator configured for operation directly by a user to dispense a medicament from the medication delivery device, wherein the operation aid is configured to be removeably attached to the medication delivery device to alleviate the direct operation of the actuator by the user, the operation aid comprising:
an attachment element defining a sleeve configured to receive at least a portion of a body of the medicament delivery device;
an actuation element;
a spring arranged between the actuation element and the sleeve; and
a transmitter element;
wherein the actuation element and the transmitter element are operably connected to the actuator such that when the actuation element is moved from a first position to a second position by a user the transmitter element is moved from a first position to a second position, wherein the transmitter element directly contacts the actuator and exerts a force on the actuator thereby moving the actuator from a first position to a second position;
wherein the medicament is caused to be delivered from the medication delivery device;
wherein the spring biases the operation aid such that when the actuation element is released by the user while the medication delivery device remains attached to the operation aid the actuation element returns from its second position to its first position and the transmitter element returns from its second position to its first position;
wherein the medication delivery device is an auto injector; and
wherein a force required for delivering the medicament from the medication delivery device is provided by a device spring of the medication delivery device.

2. The system of claim 1, wherein the actuator comprises a button being located at the proximal end of the device.

3. The system of claim 1, being configured to reduce a force required to operate the medication delivery device.

4. The system of claim 1, wherein the actuation element is operable by a user.

5. The system of claim 1, wherein the actuation element comprises a lever mechanism.

6. The system of claim 1, wherein the actuation element comprises a gear mechanism.

7. The system of claim 1, being configured to facilitate the actuation of the medication delivery device from a direction which is inclined to a moving direction of the actuator.

8. The system of claim 1, wherein the medication delivery device is a pen-type medication delivery device.

9. The system of claim 1, wherein the actuator of the medication delivery device comprises a button.

10. The system of claim 1, wherein the actuator is located at a proximal end of the medication delivery device.

11. The system of claim 1, wherein the operation aid is configured such that it at least partly covers the actuator of the medication delivery device when the operation aid is attached to the medication delivery device.

12. The system of claim 1, wherein when the sleeve receives the at least a portion of the body of the medication delivery device, the sleeve surrounds the actuator of the medication delivery device.

13. A system comprising an operation aid for a medication delivery device configured to alleviate the operation of an actuator of the medication delivery device, wherein the operation aid comprises:
an attachment element defining a sleeve configured to receive at least a portion of a body of the medication delivery device
an actuation element operable by a user;
a spring arranged between the actuation element and the sleeve; and
a transfer mechanism to transfer a movement of the actuation element into a movement of the actuator of the medication delivery device, the transfer mechanism comprises a transmitter element which exerts a force on the actuator of the medication delivery device when the actuation element is operated;
wherein the actuation element and the transmitter element are coupled by a lever mechanism to achieve a mechanical advantage between the actuation element and the transmitter element to reduce the force required to operate the actuator of the medication delivery device, where the mechanical advantage can be adapted by the user;
wherein the system further comprises the medication delivery device, the operation aid being removeably attachable to the medication delivery device; and
wherein the medication delivery device is an auto injection, wherein a force required for delivering a medicament from the medication delivery device is provided by a device spring of the medication delivery device.

14. The operation aid of claim 13, wherein when the sleeve receives the at least a portion of the body of the medication delivery device, the sleeve surrounds the actuator of the medication delivery device.

* * * * *